(12) United States Patent
Nagase (10) Patent No.: US 9,411,150 B2
(45) Date of Patent: Aug. 9, 2016

(54) ENDOSCOPE IMAGE PICKUP UNIT (71) Applicant: OLYMPUS CORPORATION, Tokyo (JP)

(72) Inventor: Masatoshi Nagase, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/751,923

(22) Filed: Jun. 26, 2015

(65) Prior Publication Data

US 2015/0293343 A1 Oct. 15, 2015

Related U.S. Application Data

(63) Continuation of application No. PCT/JP2014/061889, filed on Apr. 28, 2014.

(30) Foreign Application Priority Data

Aug. 5, 2013 (JP) ................................. 2013-162449

(51) Int. Cl.
*A61B 1/04* (2006.01)
*H04N 9/47* (2006.01)
*H04N 7/18* (2006.01)
*G02B 23/24* (2006.01)
*A61B 1/05* (2006.01)
*H04N 5/335* (2011.01)
*H04N 5/225* (2006.01)

(52) U.S. Cl.
CPC ............ *G02B 23/2484* (2013.01); *A61B 1/051* (2013.01); *H04N 5/2253* (2013.01); *H04N 5/335* (2013.01); *H04N 2005/2255* (2013.01)

(58) Field of Classification Search
CPC ............... A61B 1/00064; A61B 1/051; G02B 23/2484; H04N 5/335; H04N 5/2253
USPC ............................................................ 348/76
See application file for complete search history.

(56) References Cited

FOREIGN PATENT DOCUMENTS

| JP | S63-68128 A | 3/1988 |
| JP | 2007-073958 A | 3/2007 |
| JP | 2013-098182 A | 5/2013 |
| JP | 2013-123628 A | 6/2013 |

OTHER PUBLICATIONS

International Search Report dated Aug. 5, 2014 issued in PCT/JP2014/061889.

*Primary Examiner* — Mehrdad Dastouri
*Assistant Examiner* — Kristin Dobbs
(74) *Attorney, Agent, or Firm* — Scully, Scott, Murphy & Presser, PC (57) ABSTRACT

In an endoscope image pickup unit including an image pickup device having connecting terminal portions on a back surface, and a flexible printed wiring board having a first region on which the image pickup device is mounted, a second region in which an external connection portion for connecting an electric cable is formed, a bent portion provided between the first region and the second region, and two conductive layers, input and output pads for performing input of a voltage to and input and output of signals to and from the image pickup device are disposed at a position closer to the bent portion than ground pads for connecting the image pickup device to a ground, and input and output wirings to be connected to the input and output pads are formed from a same conductive layer as the input and output pads.

2 Claims, 9 Drawing Sheets

ENDOSCOPE IMAGE PICKUP UNIT

CROSS REFERENCE TO RELATED APPLICATION

This application is a continuation application of PCT/JP2014/061889 filed on Apr. 28, 2014 and claims benefit of Japanese Application No. 2013-162449 filed in Japan on Aug. 5, 2013, the entire contents of which are incorporated herein by this reference.

BACKGROUND OF THE INVENTION

1. Field of the Invention

The present invention relates to an endoscope image pickup unit that is configured by an image pickup device, which has connecting terminal portions on a back surface, being mounted on a flexible printed wiring board.

2. Description of the Related Art

In order to observe spots that are difficult to observe such as interior portion of a living body, structural object, etc. for example, endoscope with image pickup units for picking up optical images is commonly used in medical and industrial field which is possible to introduce from the outside portion.

An endoscope image pickup unit is formed by including an objective lens that forms an image of an object, and an image pickup device that is placed on an image formation surface of the objective lens, and is generally called a CCD (charge-coupled device), a CMOS (complementary metal oxide-semiconductor) sensor or the like.

In order to make a mounting area on the substrate small, some image pickup devices have configurations such that connecting terminal portions for electric connection with a substrate are provided on a back surface that is opposite to a surface (a light receiving surface) on which light is incident. For example, Japanese Patent Application Laid-Open Publication No. 2007-73958 discloses a package of an image pickup device which is provided with connecting terminal portions on a back surface. If the image pickup device having the connecting terminal portions on the back surface like this is used, it is possible to make the mounting area small.

When the image pickup device having connecting terminal portions on the back surface, as disclosed in Japanese Patent Application Laid-Open Publication No. 2007-73958, is used in an endoscope image pickup unit, such a form can be adopted that the image pickup device is mounted on a flexible printed wiring board, the flexible printed wiring board is bent to be extended rearward (a direction opposite from an object) along an optical axis, and an electric cable placed in an endoscope is connected in a distal end portion of the flexible printed wiring board. As above, the flexible printed wiring board on which the image pickup device is mounted is bent and extended rearward, whereby a projected area of the outer shape of the image pickup unit onto a plane that is orthogonal to the optical axis can be made small.

SUMMARY OF THE INVENTION

An endoscope image pickup unit according to one aspect of the present invention is an endoscope image pickup unit including an image pickup device having a plurality of connecting terminal portions that are arranged on a back surface that is a surface at an opposite side from a light receiving surface, and a flexible printed wiring board including a first conductive layer and a second conductive layer on a first surface and a second surface that is opposite from the first surface, respectively, wherein the flexible printed wiring board includes a first region in which pads to be joined to the plurality of connecting terminal portions are formed, a second region in which an external connection portion for connecting an electric cable is formed, a bent portion that is provided between the first region and the second region, and bends the flexible printed wiring board with the second surface as an inner side, and wirings that electrically connect the pads and the external connection portion, the pads are configured by ground pads for connecting the image pickup device to a ground, and input and output pads that are provided closer to the bent portion than the ground pads, and are for performing input of a voltage to and input and output of signals to and from the image pickup device, and the wirings are configured by input and output wirings that electrically connect the input and output pads and the external connection portion, and are formed from the first conductive layer at least in the image pickup device mounting portion and the bent portion, and ground wirings that electrically connect the ground pads and the external connection portion, and are formed from the second conductive layer, at least in the image pickup device mounting portion and the bent portion.

DETAILED DESCRIPTION OF THE PREFERRED EMBODIMENT

Hereinafter, a preferable mode of the present invention will be described with reference to the drawings. Note that in respective drawings for use in the following explanation, a reduction scale is made to differ at each of components in order that the respective components are caused to have such sizes that the respective components are recognizable on the drawings, and the present invention is not limited only to quantities of the components, shapes of the components, ratios of the sizes of the components, and relative positional relations of the respective components, which are illustrated in these drawings.

Hereinafter, one example of an embodiment of the present invention will be described. First, with reference to FIG. 1, one example of a configuration of an endoscope 101 including an endoscope image pickup unit 1 according to the present invention will be described. Note that hereinafter, the endoscope image pickup unit 1 will be simply called an image pickup unit 1.

Figure 1:
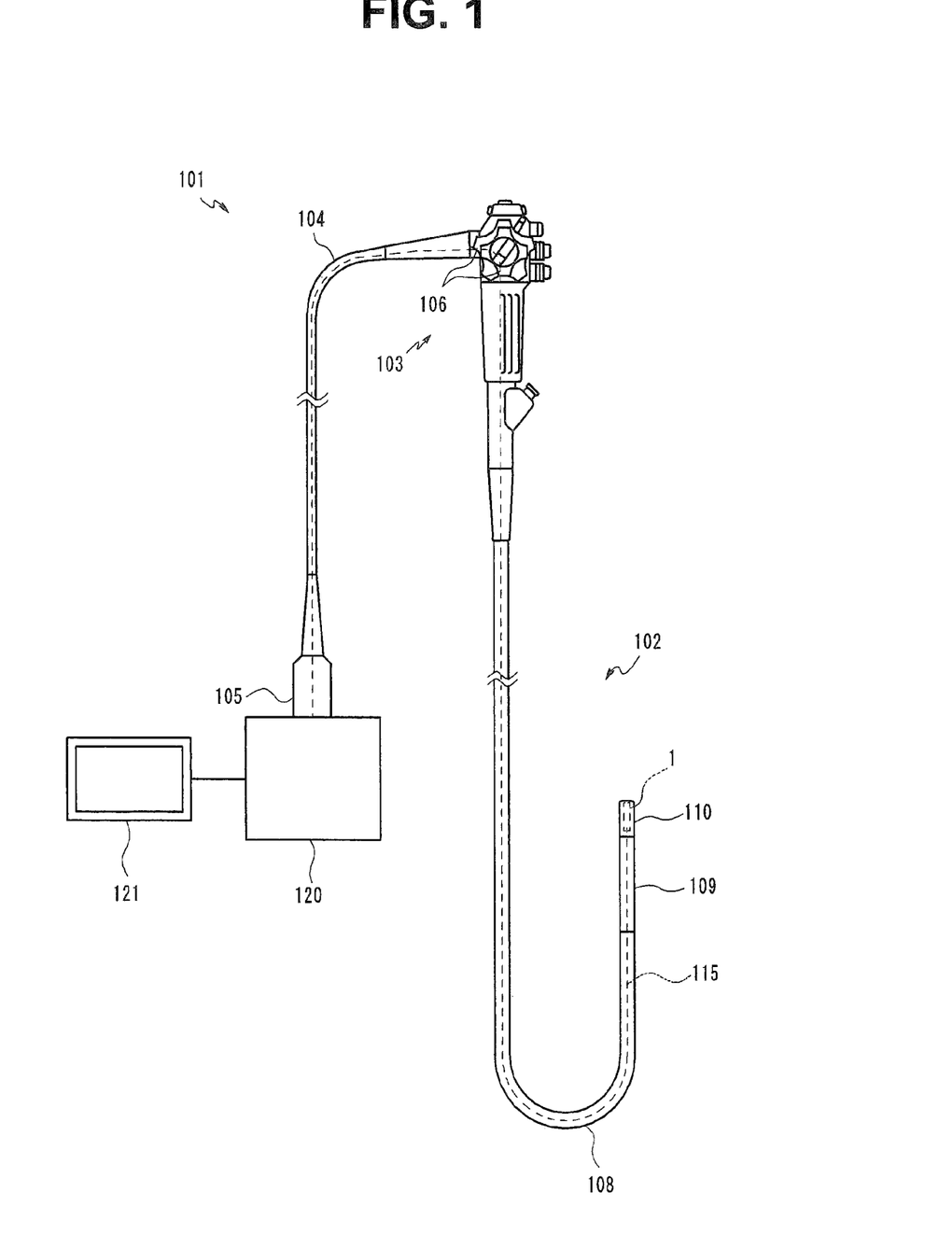
FIG. 1 is a view explaining a configuration of an endoscope.

The endoscope 101 of the present embodiment has a configuration that can be introduced into a subject such as a human body and optically picks up an image of a predetermined observed site in the subject. Note that the subject into which the endoscope 101 is introduced is not limited to a human body, and may be other living bodies, or may be artificial matters such as a machine and a building.

The endoscope 101 of the present embodiment is mainly configured by an insertion portion 102 that is introduced to an inside of a subject, an operation portion 103 that is located at a proximal end of the insertion portion 102, and a universal cord 104 that extends from a side portion of the operation portion 103, as one example.

The insertion portion 102 is configured by a distal end portion 110 that is placed at a distal end, a bending portion 109 that is placed at a proximal end side of the distal end portion 110 and bends by a remote operation, and a flexible tube portion 108 that is placed at a proximal end side of the bending portion 109, is connected to a distal end side of the operation portion 103 and has flexibility being connectively provided. Note that the endoscope 101 may have a form that is called a so-called rigid endoscope which does not include a site having flexibility in the insertion portion. Further, the endoscope 101 may have a form that does not have a bending portion that bends by a remote operation.

At the distal end portion 110, the image pickup unit 1 and an illuminating light emitting portion 113 (not illustrated in FIG. 1) are provided. Further, at the operation portion 103, an angle operation knob 106 for operating bending of the bending portion 109 is provided.

At a proximal end portion of the universal cord 104, an endoscope connector 105 which is connected to an outside apparatus 120 is provided. The outside apparatus 120 to which the endoscope connector 105 is connected is configured by including a light source section, an image processing section and an image display section 121, for example.

Further, the endoscope 101 includes an electric cable 115 and an optical fiber bundle 114 (not illustrated in FIG. 1) that are inserted through insides of the universal cord 104, the operation portion 103 and the insertion portion 102.

The electric cable 115 is configured to electrically connect the connector portion 105 and the image pickup unit 1. The connector portion 105 is connected to the outside apparatus 120, whereby the image pickup unit 1 is electrically connected to the outside apparatus 120 via the electric cable 115. Through the electric cable 115, connection to a ground (a grounding potential), and supply of electric power to the image pickup unit 1 from the outside apparatus 120, and input and output of signals between the outside apparatus 120 and the image pickup unit 1 are performed.

An image processing section that is provided in the outside apparatus 120 has a configuration that generates a video signal based on an image pickup device output signal that is outputted from the image pickup unit 1, and outputs the video signal to the image display section 121. That is to say, in the present embodiment, an optical image that is picked up by the image pickup unit 1 is displayed on the display section 121 as a video. Note that a part or all of the image processing section and the image display section 121 may be configured to be placed in the endoscope 101.

Further, the optical fiber bundle 114 is configured to transmit a light that is emitted from the light source section of the outside apparatus 120 to the illuminating light emitting portion 113 of the distal end portion 110. Note that the light source section may be configured to be placed in the operation portion 103 or the distal end portion 110 of the endoscope 101.

Figure 2:
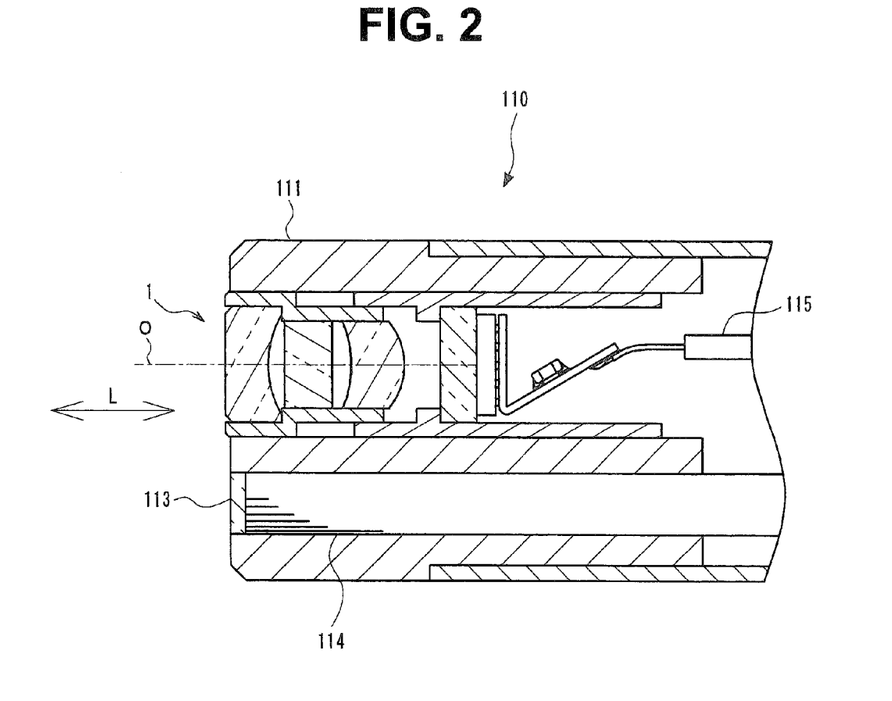
FIG. 2 is a view explaining a configuration of a distal end portion of the endoscope.

Next, a configuration of the distal end portion 110 will be described. As shown in FIG. 2, in the distal end portion 110, the image pickup unit 1 and the illuminating light emitting portion 113 are placed in a state fixed to a holding portion 111. The holding portion 111 is a rigid member that is exposed on a distal end face of the distal end portion 110.

In the present embodiment, as one example, the image pickup unit 1 is placed to pick up an image in a distal end direction along a longitudinal direction (an insertion axis direction) of the distal end portion 110 shown by an arrow L in FIG. 2. More specifically, the image pickup unit 1 is placed so that an optical axis O of the objective lens 4 which will be described later is along a longitudinal direction of the insertion portion 102. Note that the image pickup unit 1 may be placed so that the optical axis O forms a predetermined angle to the longitudinal direction of the insertion portion 102.

Further, the illuminating light emitting portion 113 has a configuration that emits a light which is emitted from the optical fiber bundle 114 to illuminate an object of the image pickup unit 1. In the present embodiment, the illuminating light emitting portion 113 is configured to emit a light to a distal end direction from the distal end face of the distal end portion 110 along the longitudinal direction of the insertion portion 102.

Figure 3:
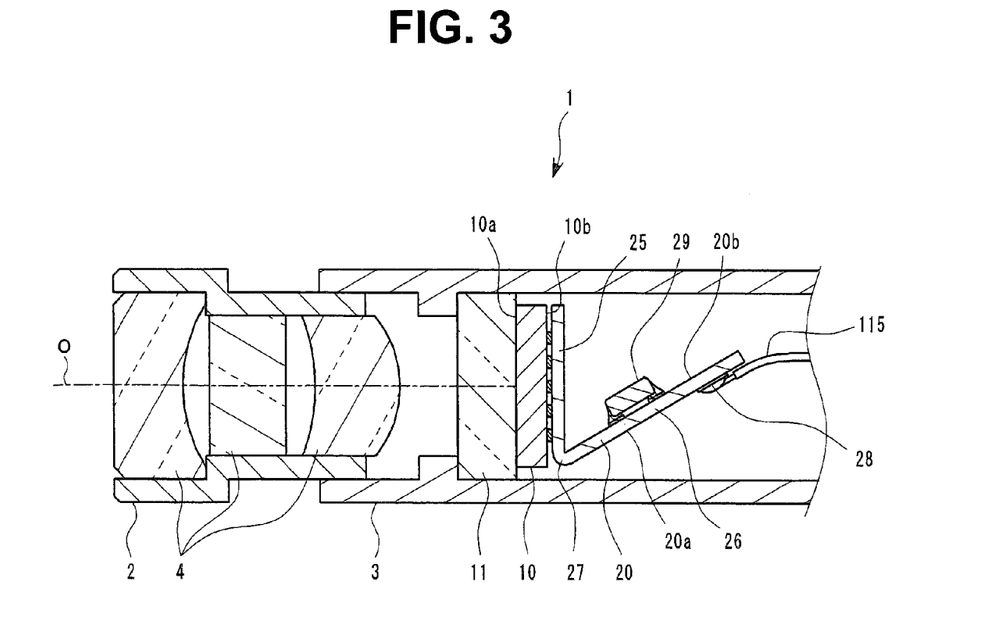
FIG. 3 is a sectional view of an image pickup unit.

Next, a configuration of the image pickup unit 1 of the present embodiment will be described. As shown in FIG. 3, the image pickup unit 1 is configured by including the objective lens 4, an image pickup device 10 and a flexible printed wiring board 20. These members that configure the image pickup unit 1 are held by a holding frame 3 substantially in a frame shape. In the present embodiment, the holding frame 3 is a cylindrical member that surrounds a periphery of the optical axis O.

Note that hereinafter, a direction (a leftward direction in FIG. 3) toward the object from the image pickup unit 1 along the optical axis O of the image pickup unit 1 will be called forward, and a direction opposite thereto will be called rearward.

The objective lens 4 is placed in a lens barrel 2 in a cylindrical shape, and is formed of one or a plurality of optical members such as lenses for forming an image of an object on a light receiving surface 10a of the image pickup device 10. Note that the objective lens 4 may be in a form of including an optical element such as a reflecting mirror, a prism, or an optical filter. Further, the objective lens 4 may be in a form having a configuration capable of changing a focal length.

The image pickup device 10 is an image sensor such as a CCD or CMOS sensor. In the present embodiment, the image pickup device 10 is fixed to a predetermined position in the holding frame 3 via a protection glass 11 that is a transparent member bonded on the light receiving surface 10a, as one example. The image pickup device 10 is placed so that the light receiving surface 10a is substantially orthogonal to the optical axis O.

Though details will be described later, the image pickup device 10 is mounted on a first surface 20a that is one surface of the flexible printed wiring board 20. A distal end portion of the electric cable 115 is connected to the flexible printed wiring board 20, and the image pickup device 10 is electrically connected to the electric cable 115 via the flexible printed wiring board 20.

A form of connection of the image pickup device 10, the flexible printed wiring board 20 and the electric cable 115 will be described hereinafter.

Figure 4:
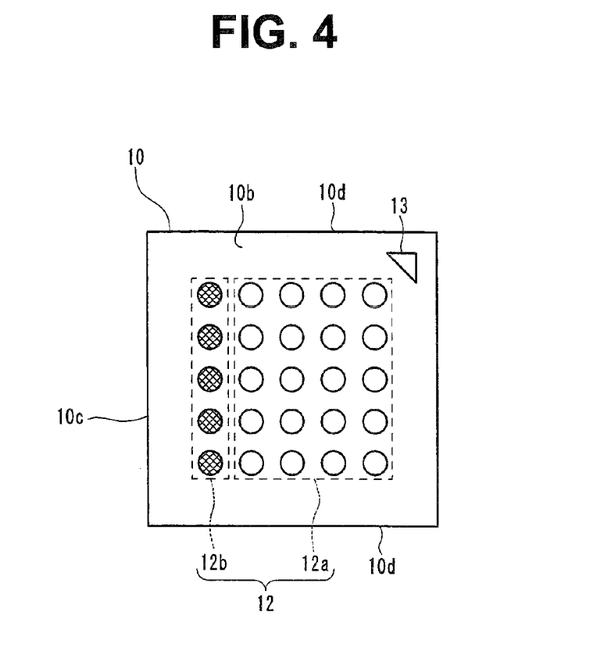
FIG. 4 is a view of an image pickup device in a state before the image pickup device is mounted, seen from a back surface side.
Figure 5:
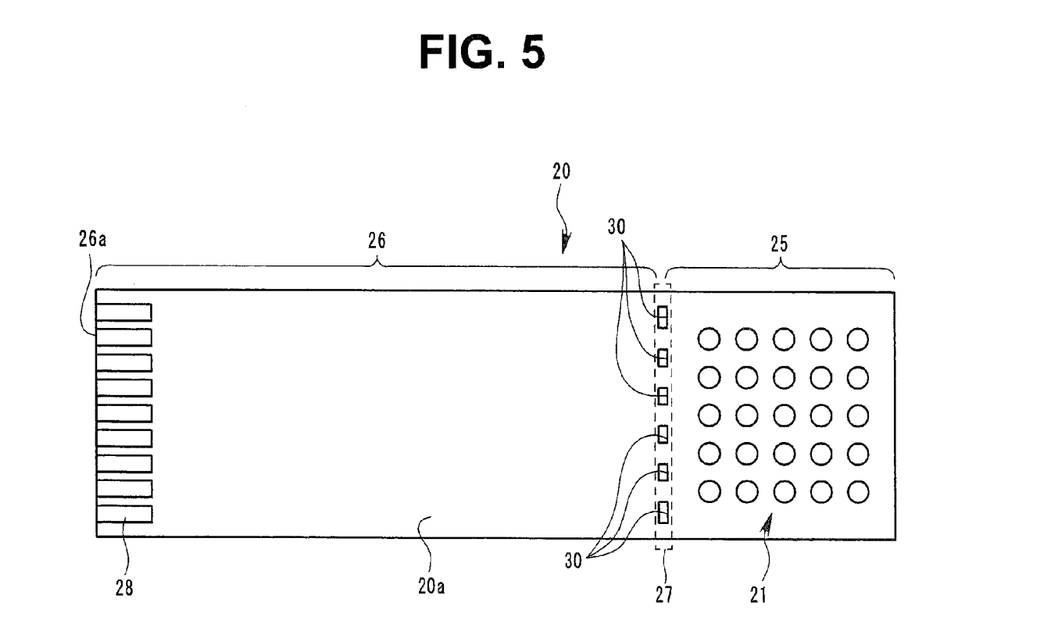
FIG. 5 is a view of a sight of a first surface in a state in which a flexible printed wiring board is developed into a planar shape.

FIG. 4 is a view of the image pickup device 10 in a state before the image pickup device 10 is mounted on the flexible printed wiring board 20, seen from a back surface 10b side. Further, FIG. 5 is a view of a sight of the first surface 20a in a state in which the flexible printed wiring board 20 is developed into a planar shape.

As shown in FIG. 4, in the image pickup device 10, a plurality of connecting terminal portions 12 formed from a conductive material such as a metal are arranged on the back surface 10b which is a surface facing in an opposite direction from the light receiving surface 10a. The image pickup device 10 has a substantially rectangular outer shape when the image pickup device 10 is seen along an axis orthogonal to the light receiving surface 10a (when the image pickup device 10 is seen along the optical axis O). In the present embodiment, the plurality of connecting terminal portions 12 are arranged in a matrix shape, and a row direction and a column direction of the matrix are substantially parallel with outer sides of the image pickup device 10 which is in a substantially rectangular shape.

The plurality of connecting terminal portions 12 of the image pickup device 10 are configured by ground terminal portions 12a that are connected to a ground, and input and output terminal portions 12b for use in input of a voltage, and input and output of signals. Note that in FIG. 4, the connecting terminal portions 12 which are shaded (crossed hatching) of the connecting terminal portions 12 are the input and output terminal portions 12b, and the others are the ground terminal portions 12a. Further, in FIG. 4, reference sign 13 denotes a mark for clarifying an orientation of the image pickup device 10. Note that the mark 13 may be in a form that is not placed in the image pickup device 10. Disposition of the ground terminal portions 12a and the input and output terminal portions 12b will be described later.

A form of a surface mounting electronic component in which a plurality of connecting terminal portions 12 are arranged on a predetermined surface of the electronic component like the image pickup device 10 of the present embodiment is generally called a BGA (ball grid array), an LGA (land grid array) or the like. The connecting terminal portions of a surface mounting electronic component in a form like this and pads of a circuit board are joined by a known technique such as metal joining such as solder jointing, a conductive adhesive or the like, and are brought into electrical conduction.

In recent years, by an art that is called a silicon through electrode (TSV: through silicon via), a plurality of connecting terminal portions can be formed on a back surface of a chip (die) having an integrated circuit which is cut out from a silicon wafer, and a mounting area of the chip having the integrated circuit can be made small.

The image pickup device 10 for use in the image pickup unit 1 for an endoscope of the present embodiment is in a size of a chip size level (a die size level) using a through silicon via as above, and the size in a case seen from a direction orthogonal to the light receiving surface 10a is approximately 3 mm square, for example.

In the present embodiment, as one example, the image pickup device 10 has a form that is called a BGA, and in a state before the image pickup device 10 is mounted, solder balls that are substantially spherical sites of solder are formed at the respective plurality of connecting terminal portions 12.

As shown in FIG. 5, on the first surface 20a of the flexible printed wiring board 20, a plurality of pads 21 that are arranged in positions corresponding to the plurality of connecting terminal portions 12 of the image pickup device 10, and are formed from a conductive material such as a metal are formed. In the present embodiment, the plurality of connecting terminal portions 12 of the image pickup device 10 and the plurality of pads 21 of the flexible printed wiring board 20 are joined by a solder jointing method, and electrical connection between both of the plurality of connecting terminal portions 12 and the plurality of pads 21 are made.

The flexible printed wiring board 20 is an electronic circuit board having flexibility. An electronic circuit board having flexibility like this is generally called an FPC (flexible printed circuit) or the like. The flexible printed wiring board 20 has a film-shaped base material formed from a material such as a resin having an electric insulating property, and has a conductive pattern formed from a conductive material such as a metal formed thereon. The material and the like configuring the flexible printed wiring board 20 are known arts, and therefore, detailed explanation thereof will be omitted.

Figure 6:
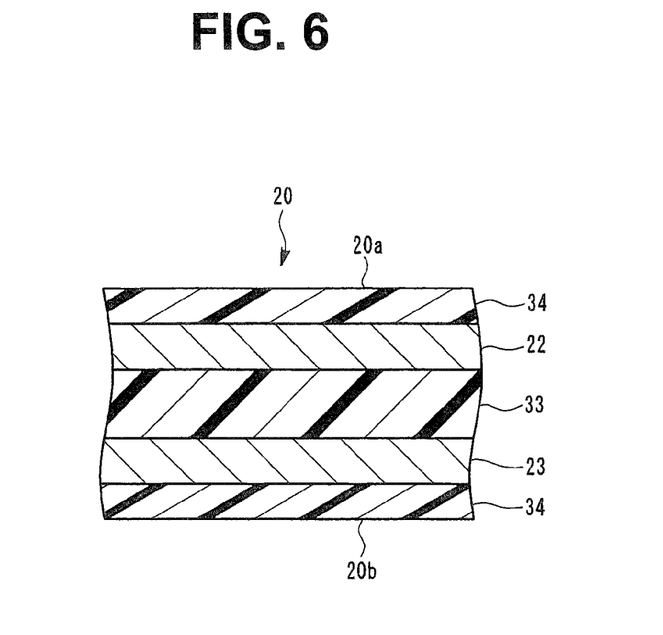
FIG. 6 is a schematic sectional view for explaining a structure of the flexible printed wiring board.

The flexible printed wiring board 20 of the present embodiment is a double-layer FPC in which conductive patterns are formed on both surfaces of the insulative base material. FIG. 6 is a schematic view of a section of a spot where conductive layers are formed on both the surfaces of the flexible printed wiring board 20.

In the flexible printed wiring board 20 of the present embodiment, a first conductive layer 22 and a second conductive layer 23 are provided on both surfaces of a film-shaped base material 33 formed from a material having an electric insulating property such as polyimide, and wirings of an electronic circuit are formed by the first conductive layer 22 and the second conductive layer, and vias that electrically connect both of the first and the second conductive layers 22 and 23.

The first conductive layer 22 is placed on the first surface 20a side on which the image pickup device 10 is mounted, and the second conductive layer 23 is placed on the second surface 20b side at an opposite side from the first surface 20a. That is to say, the plurality of pads 21 described above are formed by a part of the first conductive layer 22. Further, FIG. 6 shows an insulating layer 34 that is formed on the respective first conductive layer 22 and second conductive layer 23. Note that it goes without saying that the insulating layer 34 is not formed at spots to which other electronic components such as the pads 21 are joined.

As shown in FIG. 5, the flexible printed wiring board 20 is configured by having two regions that are an image pickup device mounting portion 25 on which the image pickup device 10 is mounted, and one or a plurality of extending portions 26 extending from one or a plurality of outer sides with the one or the plurality of outer sides of the image pickup device mounting portion 25 as a proximal end or proximal ends.

Further, as shown in FIG. 3, the flexible printed wiring board 20 in the state in which the image pickup device 10 is mounted thereon is placed in the image pickup unit 1 in a state in which a bent portion 27 is formed between the image pickup device mounting portion 25 and the extending portion 26.

In the image pickup device mounting portion 25, the plurality of pads 21 to which the plurality of connecting terminal portions 12 of the image pickup device 10 are joined are formed on the first surface 20*a*, as described above. An outer shape of the image pickup device mounting portion 25 is not specially limited if only the outer shape is a shape in which the pads 21 and wirings which will be described later can be formed, but in a case where the outer shape is projected on a plane parallel with the light receiving surface 10*a* of the image pickup device 10, the outer shape of the image pickup device mounting portion 25 is preferably a shape that is substantially equivalent to the outer shape of the image pickup device 10, or is not outside from the outer shape of the image pickup device 10.

In the present embodiment, as one example, the outer shape of the image pickup device mounting portion 25 is a substantially parallelogram, and four outer sides of the image pickup device mounting portion 25 are substantially parallel with the outer sides of the image pickup device 10 to be mounted. A projection shape of the outer shape of the image pickup device mounting portion 25 onto a plane parallel with the light receiving surface 10*a* of the image pickup device 10 is smaller than a projection shape of the outer shape of the image pickup device 10 onto the same plane. That is to say, in a case in which the image pickup unit 1 is seen from a front along the optical axis O, the image pickup device mounting portion 25 has a shape which is hidden behind the image pickup device 10.

Making the outer shape of the image pickup device mounting portion 25 substantially equivalent to or smaller than the outer shape of the image pickup device 10 as above contributes to reducing the projection area of the outer shape of the image pickup unit 1 having the image pickup device mounting portion 25 and the image pickup device 10 to a plane orthogonal to the optical axis O. Note that the outer shape of the image pickup device mounting portion 25 may be larger than the outer shape of the image pickup device 10.

As shown in FIG. 5, the extending portion 26 is formed to extend from one of the outer sides of the image pickup device mounting portion 25 to a direction substantially orthogonal to the outer side, when the flexible printed wiring board 20 is brought into a state developed into a planar shape (a state before the bent portion is formed).

A width of the extending portion 26 is substantially the same as a width of the image pickup device mounting portion 25 which is located at a proximal end of the extending portion 26 or is smaller than the width of the image pickup device mounting portion 25. In the present embodiment, as one example, the extending portion 26 has the same width as the width of the image pickup device mounting portion 25. A length of the extending portion 26 is not specially limited, but is set in accordance with an area that is necessary to dispose an external connection portion 28, an electronic component 29 and wirings that will be described later.

The external connection portion 28 is formed at a distal end portion 26*a* of the extending portion 26. The external connection portion 28 is configured so that the distal end portion of the electric cable 115 is connectable to the external connection portion 28. The external connection portion 28 and the electric cable 115 are connected, whereby the electronic circuit formed on the flexible printed wiring board 20 including the image pickup device 10, and the electric cable 115 are electrically connected.

A form of connection of the external connection portion 28 and the electric cable 115 is not specially limited. Connection of the external connection portion 28 and the electric cable 115 may be by solder jointing or may be a detachable connector mechanism, for example.

In the present embodiment, as one example, connection of the external connection portion 28 and the electric cable 115 is solder jointing, and the external connection portion 28 is configured by a plurality of pads that are connected to the electronic circuit formed on the flexible printed wiring board 20 including the image pickup device 10 and are formed from a conductive material.

Note that the external connection portion 28 of the present embodiment which is illustrated is formed on the first surface 20*a* of the flexible printed wiring board 20, but the external connection portion 28 may be formed on the second surface 20*b*, or may be formed on both the first surface 20*a* and the second surface 20*b*.

Further, on the extending portion 26, one or a plurality of electronic components 29 are mounted in accordance with necessity. The electronic component 29 in the present embodiment is a capacitor that is placed for the purpose of restraining a variation in a power supply voltage of the image pickup device 10 and restraining noise in power supply wiring. Note that the extending portion 26 may have a form in which a plurality of electronic components are mounted, or may have a form in which an electronic component is not mounted. Further, when the electronic component 29 is mounted on the extending portion 26, the electronic component 29 may have a form of being mounted on either one of the first surface 20*a* and the second surface 20*b*.

The bent portion 27 is formed by the flexible printed wiring board 20 being folded with the second surface 20*b* as an inner side, in a boundary portion of the image pickup device mounting portion 25 and the extending portion 26. In other words, the bent portion 27 is a site where the flexible printed wiring board 20 is folded along the outer side of the image pickup device mounting portion 25 at which the extending portion 26 is provided, with the second surface 20*b* as the inner side.

The bent portion 27 is formed, whereby the extending portion 26 extends so that the distal end portion 26*a* heads toward a rear side of the image pickup unit 1, in the image pickup unit 1. In other words, the extending portion 26 in the image pickup unit 1 extends toward a side opposite from the light receiving surface 10*a* from the back surface 10*b* of the image pickup device 10 along an axis orthogonal to the light receiving surface 10*a*.

Further, in other words, the flexible printed wiring board 20 on which the image pickup device 10 is mounted is configured by having the bent portion 27 which is bent with the second surface 20*b* at an opposite side from the first surface 20*a* on which the image pickup device 10 is mounted as the inner side, the image pickup device mounting portion 25 which is one of sides sandwiching the bent portion 27 and is a region on which the image pickup device 10 is mounted, and the extending portion 26 which is the other one of the sides sandwiching the bent portion 27 and extends in the direction toward the side opposite from the light receiving surface 10*a* from the back surface 10*b* of the image pickup device 10 along the axis orthogonal to the light receiving surface 10*a* from the bent portion 27.

An angle (an internal angle) that is formed by the image pickup device mounting portion 25 and the extending portion 26 in the bent portion 27 is not specially limited, and may be an acute angle, may be a right angle, or may be an obtuse angle. For example, when the angle which is formed by the image pickup device mounting portion 25 and the extending portion 26 in the bent portion 27 is made a right angle or an acute angle as in the present embodiment which is illustrated, the outer shape of the extending portion 26 in the case of the outer shape being projected on the plane parallel with the light receiving surface 10*a* of the image pickup device 10 coincides with the outer shape of the image pickup device 10. This means that the projection area of the image pickup unit 1 onto the plane orthogonal to the optical axis O can be reduced in other words.

In the present embodiment, as one example, a folding angle of the bent portion 27 is an acute angle, and the folding angle of the bent portion 27 is set so that a whole of the extending portion 26 is hidden by the image pickup device 10 when the extending portion 26 is seen from the front side along the optical axis O. In other words, in the image pickup unit 1 of the present embodiment, the outer shape of the flexible printed wiring board 20 lies within the outer shape of the image pickup device 10 when the outer shape of the flexible printed wiring board 20 is projected onto the plane parallel with the light receiving surface 10$a$ of the image pickup device 10.

Further, as shown in FIG. 5, in the flexible printed wiring board 20, a plurality of slits 30 are formed along the bent portion 27. The slits 30 are through-holes provided by being bored by avoiding wirings that are formed in the flexible printed wiring board 20 and will be described later, and are provided to facilitate folding in the case of the bent portion 27 being formed on the flexible printed wiring board 20.

As described above, the image pickup unit 1 of the present embodiment has the flexible printed wiring board 20 on which the image pickup device 10 is mounted, and the flexible printed wiring board 20 is electrically connected to the electric cable 115 which extends from the image pickup unit. The flexible printed wiring board 20 has the image pickup device mounting portion 25 on which the image pickup device 10 is mounted, and the extending portion 26 which extends from the outer side of the image pickup device mounting portion 25 and has the external connection portion 28 to which the electric cable 115 is connected. In the flexible printed wiring board 20, the bent portion 27 is formed between the image pickup device mounting portion 25 and the extending portion 26. The extending portion 26 is placed to be substantially hidden behind the outer shape of the image pickup device 10 when the image pickup device 10 is seen from the light receiving surface side along the axis orthogonal to the light receiving surface 10$a$.

Next, details of the plurality of connecting terminal portions 12 of the image pickup device 10, the plurality of pads 21 and the wirings which are formed on the flexible printed wiring board 20 will be described.

As shown in FIG. 4, the plurality of connecting terminal portions 12 of the image pickup device 10 are configured by the ground terminal portions 12$a$ which are connected to the ground, and the input and output terminal portions 12$b$ which are used in input of a voltage, and input and output of signals.

In a set of all the connecting terminal portions 12 which are provided in the image pickup device 10, the input and output terminal portions 12$b$ are placed along predetermined one or a plurality of outer sides of the substantially parallelogram-shaped image pickup device 10 which is or are outermost perimeter portion or portions of the set. Here, the predetermined one or the plurality of outer sides refer to a side 10$c$ that is close to the bent portion 27, and two sides 10$d$ that intersect the side 10$c$ in the case of the image pickup device 10 being mounted on the flexible printed wiring board 20.

Figure 7:
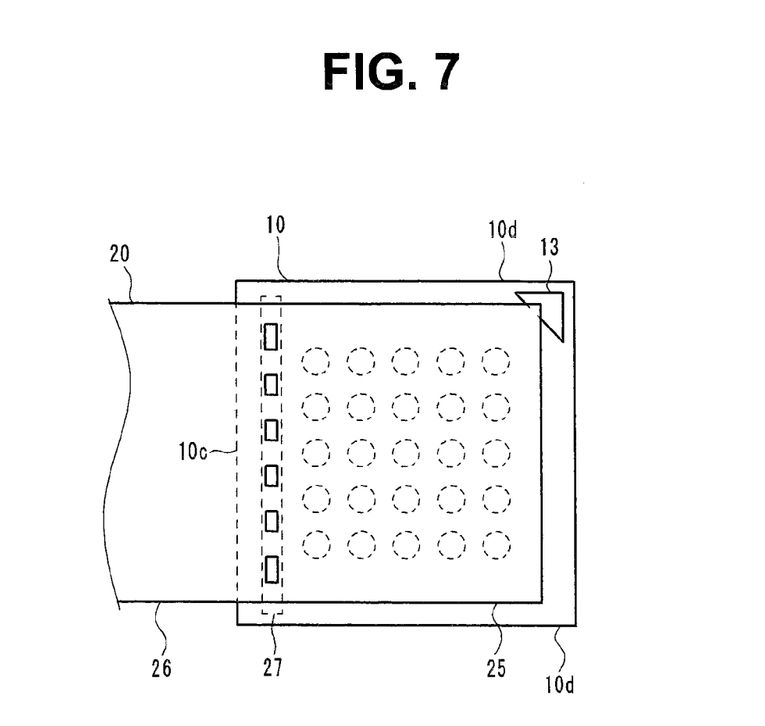
FIG. 7 is a view of the flexible printed wiring board on which the image pickup device is mounted, seen from a second surface side.

FIG. 7 is a view of the flexible printed wiring board 20 on which the image pickup device 10 is mounted, seen from the second surface 20$b$ side. As shown in FIG. 7, in the flexible printed wiring board 20 of the present embodiment, the bent portion 27 is formed in one spot, and the input and output terminal portions 12$b$ are arranged in one row at the outermost perimeter portion, along the one side 10$c$ of the image pickup device 10 which is the closest to the bent portion 27 and is substantially parallel with the bent portion 27.

The ground terminal portions 12$a$ are disposed at spots where the aforementioned input and output terminal portions 12$b$ are not disposed. That is to say, the ground terminal portions 12$a$ are not disposed in the region which is close to the bent portion 27 in a state in which the image pickup device 10 is mounted on the flexible printed wiring board 20. Further, in other words, the ground terminal portions 12$a$ are disposed to sandwich the input and output terminal portions 12$b$ between the ground terminal portions 12$a$ and the bent portion 27, in the state in which the image pickup device 10 is mounted on the flexible printed wiring board 20. Note that some of the ground terminal portions 12$a$ may be disposed at the outermost perimeter portion at which the input and output terminal portions 12$b$ are arranged.

Figure 8:
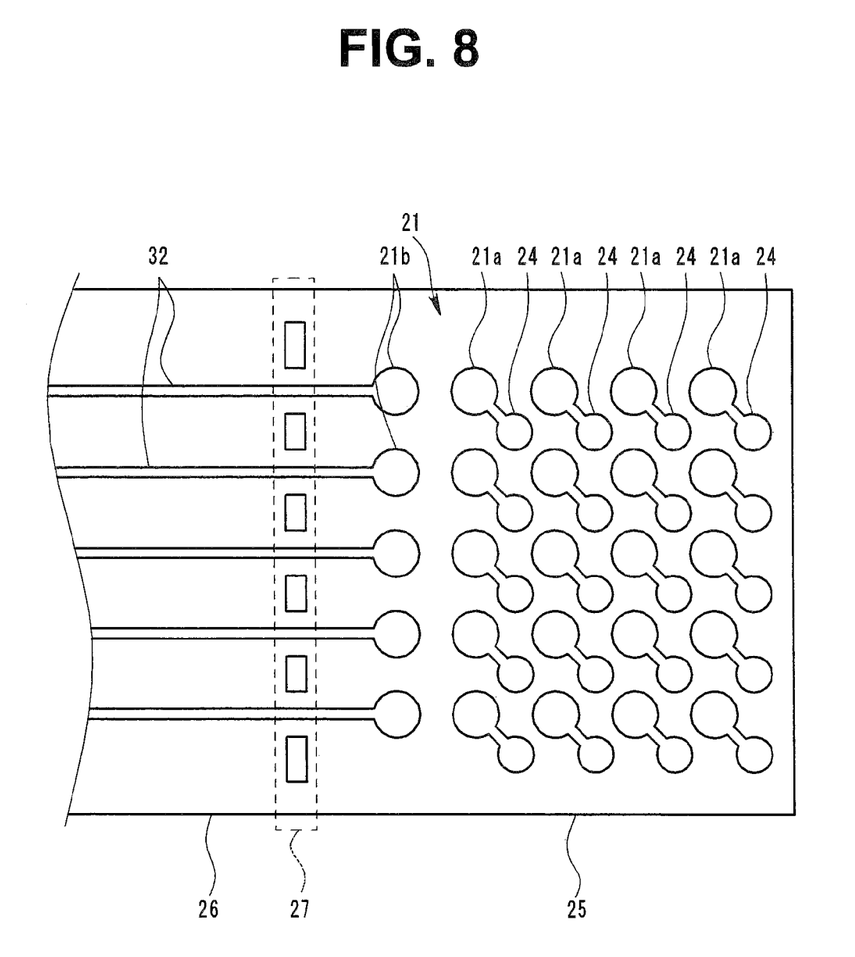
FIG. 8 is a view showing a shape of a first conductive layer provided on the first surface side of the flexible printed wiring board.

FIG. 8 is a view showing a shape of the first conductive layer 22 which is provided on the first surface 20$a$ side in the state in which the flexible printed wiring board 20 is developed. As shown in FIG. 8, the pads 21 of the flexible printed wiring board 20 are configured by ground pads 21$a$ and input and output pads 21$b$ to which the ground terminal portions 12$a$ and the input and output terminal portions 12$b$ of the image pickup device 10 are respectively joined.

As described above, the input and output terminal portions 12$b$ of the image pickup device 10 are disposed at the side close to the bent portion 27, of an outer perimeter of an array of the connecting terminal portions 12. Accordingly, the input and output pads 21$b$ of the pad 21 are similarly disposed on the side which is the outermost perimeter and along the bent portion 27 of a group formed of all the pads 21. Further, the ground pads 21$a$ are placed at spots at which the input and output pads 21$b$ are not placed.

Next, a configuration of electric connection of the pads 21 provided at the image pickup device mounting portion 25 and the external connection portion 28 which is provided at the extending portion 26, in the flexible printed wiring board 20, will be described.

The flexible printed wiring board 20 has the two conductive layers of the first conductive layer 22 provided at the first surface 20$a$ side, and the second conductive layer 23 provided at the second surface side 23, as described above.

The pads 21 which are formed of the ground pads 21$a$ and the input and output pads 21$b$ are formed from the first conductive layer 22. As shown in FIG. 8, input and output wirings 32 that are wirings for electrically connecting the input and output pads 21$b$ and the external connection portion 28 are formed from the first conductive layer 22 which is provided at the first surface 20$a$ side, in a range extending to a predetermined position of the extending portion 26 with at least the individual input and output pads 21$b$ as proximal ends.

Here, the predetermined range in which the input and output wiring 32 is formed from the first conductive layer 22 is from the input and output pad 21$b$ to a region on which the electronic component 29 is mounted, in the case where the electronic component 29 is mounted on the extending portion 26. Further, when the electronic component 29 is not mounted on the extending portion 26, the predetermined range in which the input and output wiring 32 is formed from the first conductive layer 22 is from the input and output pad 21$b$ to a region where the external connection portion 28 is formed. In the regions where the electronic component 29 and the external connection portion 28 are formed, the input and output wiring 32 is disposed in accordance with these forms, and therefore, the conductive layer which configures the input and output wiring 32 may be the first conductive layer 22 or may be the second conductive layer 23.

That is to say, in the present embodiment, the input and output wiring 32 which is connected to the input and output pad 21b is formed from the first conductive layer 22 similarly to the input and output pad 21b, at least in a range in which the input and output wiring 32 passes the bent portion 27 after being drawn out from the input and output pad 21b and extends by a predetermined distance toward the distal end portion 26a of the extending portion 26. In a range which is separated from the bent portion 27 in the extending portion 26 more than the predetermined distance to the distal end portion 26a side of the extending portion 26, the conductive layer which forms the input and output wiring 32 is not specially limited.

Figure 9:
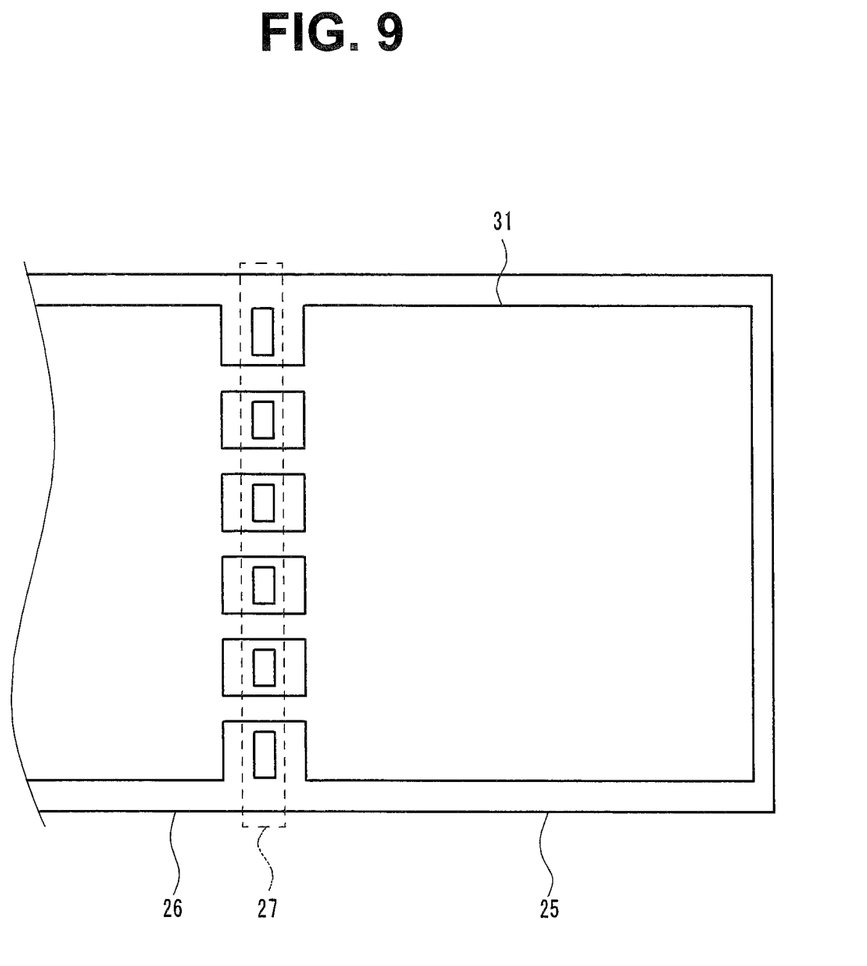
FIG. 9 is a view showing a shape of a second conductive layer provided on a second surface side of the flexible printed wiring board.

FIG. 9 is a view showing a shape of the second conductive layer 23 which is provided at the second surface 20b side, in the state in which the flexible printed wiring board 20 is developed. As shown in FIG. 9, a ground wiring 31 which is a wiring for electrically connecting the ground pads 21a and the external connection portion 28 is formed from the second conductive layer 23 which is provided at the second surface 20b side, at least in a range reaching a predetermined position of the extending portion 26 with the individual ground pads 21a as proximal ends.

Here, the predetermined range in which the ground wiring 31 is formed from the second conductive layer 23 is from the ground pads 21a to a region on which the electronic component 29 is mounted when the electronic component 29 is mounted on the extending portion 26. Further, when the electronic component 29 is not mounted on the extending portion 26, the predetermined range in which the ground wiring 31 is formed from the second conductive layer 21 is from the ground pads 21a to a region in which the external connection portion 28 is formed. In the regions in which the electronic component 29 and the external connection portion 28 are formed, the ground wiring 31 is disposed in accordance with the forms thereof, and therefore, the conductive layer that configures the ground wiring 31 may be the first conductive layer 22 or may be the second conductive layer 23.

The ground wiring 31 which is formed from the second conductive layer 23, and the ground pads 21a which are formed from the first conductive layer 22 are electrically connected by columnar vias 24 (illustrated in FIG. 8) that are formed from a conductive material such as a metal and penetrate through the flexible printed wiring board 20. Note that an art for establishing electric connection between the two conductive layers in the flexible printed wiring board 20 having the two conductive layers is known, and detailed explanation thereof will be omitted. Note that the ground wiring 31 and the ground pads 21a may be in a form in which the ground wiring 31 and the ground pads 21a are electrically connected by an art that is called pad on via.

That is to say, in the present embodiment, the ground wiring 31 which is connected to the ground pads 21a is formed from the second conductive layer 23 which is provided at an opposite side from the ground pads 21a, at least in the range in which the ground wiring 31 passes the bent portion 27 from the image pickup device mounting portion 25 and extends by the predetermined distance toward the distal end portion 26a of the extending portion 26. In the range which is separated from the bent portion 27 in the extending portion 26 more than the predetermined distance to the distal end portion 26a side of the extending portion 26, the conductive layer which forms the input and output wiring 32 is not specially limited.

Further, in the present embodiment, as shown in FIG. 9, the ground wiring 31 is formed into a planar shape to cover an opposite side from the region where the pads 21 are formed, in the image pickup device mounting portion 25. The ground wiring 31 is formed to cover the opposite side from the region where the pads 21 are formed, whereby all the ground terminal portions 12a of the image pickup device 10 can be connected to the ground.

As in the present embodiment described above, in the image pickup unit 1 in which a reflection surface is not provided on the objective lens 4 and the optical axis O does not bend halfway, reducing the outer shape and the mounting area of the image pickup device 10 contributes to reducing the projection area of the outer shape of the image pickup unit 1 onto the plane orthogonal to the optical axis O.

In the present embodiment, the image pickup device 10 is caused to have the form having the connecting terminal portions 12 on the back surface 10b, whereby the mounting area of the image pickup device 10 is reduced, and the bent portion 27 is provided at the flexible printed wiring board 20 and the extending portion 26 is caused to extend toward the rear side of the image pickup device 10, whereby the external connection portion 28 is disposed to be hidden behind the image pickup device 10 when the image pickup device 10 is seen from the front side along the optical axis O. The flexible printed wiring board 20 is a circuit board having the two conductive layers that are the first conductive layer 22 at the first surface 20a side where the pads 21 to which the image pickup device 10 is joined is provided, and the second conductive layer 23 at the second surface 20b side which is opposite from the first surface 20a.

Here, in the present embodiment, in the pads 21 to which the image pickup device 10 is mounted, the input and output pads 21b are provided close to the bent portion 27 in the outermost perimeter of the group of the pads 21. In other words, in the present embodiment, on the flexible printed Wiring board 20, the input and output pads 21b are disposed at the outer perimeter portion which is close to the external connection portion 28 in the group of the pads 21.

Accordingly, in the present embodiment, as shown in FIG. 8, the input and output wirings 32 which electrically connect the input and output pads 21b and the external connection portion 28 can be formed from the single first conductive layer 22 without being caused to pass among the pads 21 adjacent to one another, and spaces among the pads 21 can be made small. As above, in the present embodiment, the spaces (center distances) of the connecting terminal portions 12 of the image pickup device 10 can be made small, and therefore, the image pickup device 10 can be made compacter.

Further, since the flexible printed wiring board 20 of the present embodiment is in the form which has the two conductive layers, a radius of curvature of the bent portion 27 can be made small, and the bent portion 27 can be disposed to be hidden inside the outer shape of the image pickup device 10, or a protruding amount of the bent portion 27 from the outer shape of the image pickup device 10 can be made very small, when the image pickup device 10 is seen from the front side.

As described above, according to the present embodiment, the relatively thin flexible printed wiring board 20 having the two conductive layers can be used, while the compact image pickup device 10 in which the disposition spaces among the connecting terminal portions 12 are small is adopted. Therefore, according to the present embodiment, the projection area of the outer shape of the endoscope image pickup unit 1 formed by including the image pickup device 10 having the connecting terminal portions 12 on the back surface 10b, onto the plane orthogonal to the optical axis O can be made small.

Further, in the present embodiment, the input and output pads 21b are disposed at the outer perimeter portion close to the external connection portion 28 in the group of the pads 21, as shown in FIG. 8, and therefore, the input and output wirings 32 do not have to be placed to detour a periphery of the group of the pads 21. In other words, all the input and output wirings 32 are rectilinearly placed toward the external connection portion 28 from the input and output pads 21b. Further, in the present embodiment, all the ground wirings 31 are formed from the second conductive layer 23 at the second surface 20b side in the image pickup device mounting portion 25, and therefore, the ground wiring 31 does not have to be placed to detour the periphery of the group of the pads 21, either.

Since in the present embodiment, no wiring detours the periphery of the group of the pads 21 in the image pickup device mounting portion 25 like this, the outer shape of the image pickup device mounting portion 25 can be made small, and the image pickup device mounting portion 25 can be disposed to be hidden inside the outer shape of the image pickup device 10, or the protruding amount of the image pickup device mounting portion 25 from the outer shape of the image pickup device 10 can be made very small. This contributes to reducing the projection area of the outer shape of the endoscope image pickup unit 1 onto the plane orthogonal to the optical axis O.

Further, in the present embodiment, all the ground pads 21a are connected to the ground wiring 31 on the second surface 20b side via the vias 24, but the ground pads 21a and the vias 24 are placed to sandwich the input and output pads 21b with the bent portion 27. In other words, in the present embodiment, the ground pads 21a accompanied by the vias 24 are placed at the positions farther away from the bent portion 27 than the input and output pads 21b without connection by vias. In general, a portion provided with a via which penetrates through a base material in a flexible printed wiring board is easily broken when a bending stress is applied to the flexible printed wiring board. In the present embodiment, bending stress at a time of forming the bent portion 27 is difficult to apply to the portions where the vias 24 are formed, and therefore, breakage of the flexible printed wiring board 20 can be prevented.

Note that in the aforementioned embodiment, the input and output terminal portions 12b of the image pickup device 10 are only provided at the outer perimeter along the one side 10c which is the closest to the bent portion 27 and is substantially parallel with the bent portion 27, of the outer sides of the image pickup device 10, but the input and output terminal portions 12b may be in a form in which the input and output terminal portions 12b are provided along a plurality of sides.

Figure 10:
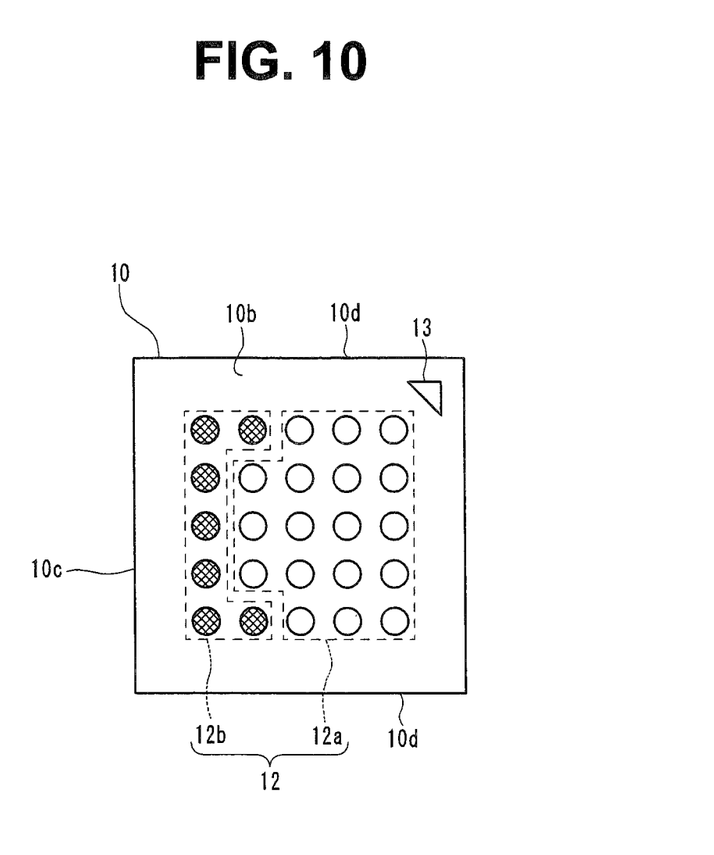
FIG. 10 is a view showing disposition of input and output terminal portions of an image pickup device, in a first modification.
Figure 11:
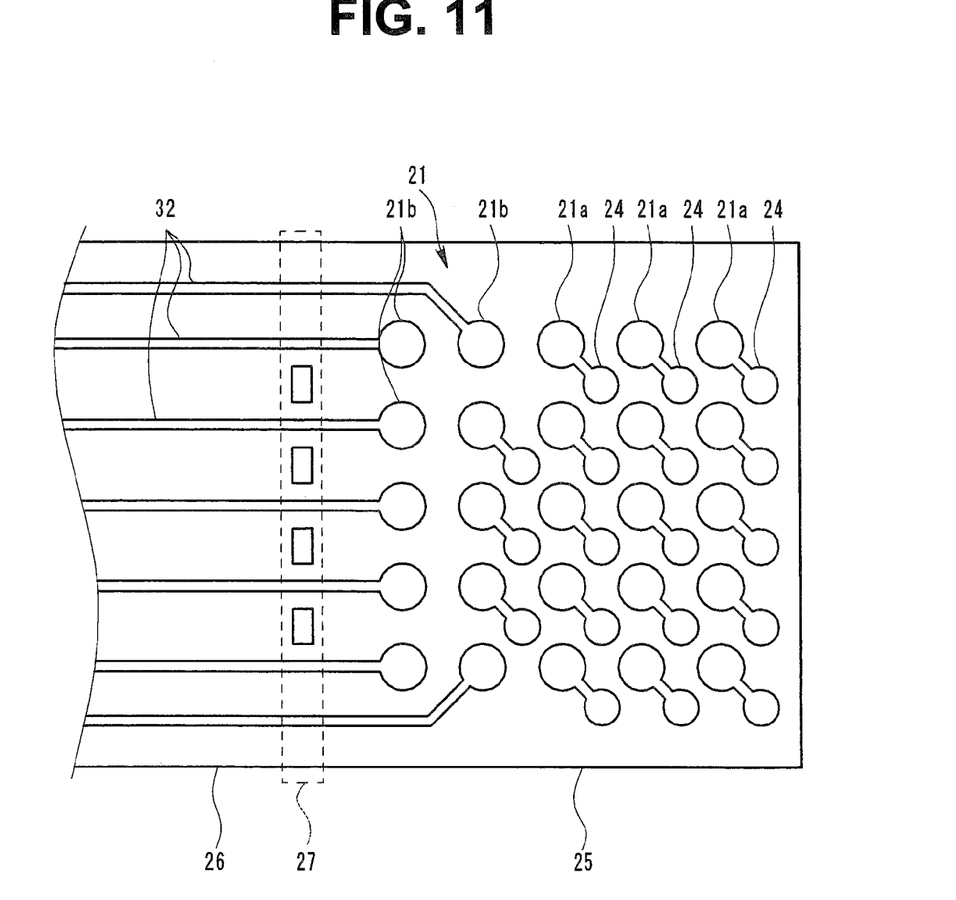
FIG. 11 is a view showing disposition of pads and input and output wirings, in the first modification.

For example, as shown in FIG. 10 as a first modification, the input and output terminal portions 12b of the image pickup device 10 may be in a form in which the input and output terminal portions 12b are formed at an outermost perimeter of the group of the connecting terminal portions 12 along the side 10c which is close to the bent portion 27 and the two sides 10d which intersect the side 10c, when the image pickup device 10 is mounted on the flexible printed wiring board 20. In the first modification, the input and output wirings 32 corresponding to the input and output terminal portions 12b which are disposed along the sides 10d, out of the input and output wirings 32 of the flexible printed wiring board 20, are disposed along an outer side of the group of the pads 21 as shown in FIG. 11.

Further, in the aforementioned embodiment, only the one extending portion 26 of the flexible printed wiring board 20 is adopted, but such a form may be adopted that a plurality of extending portions 26 are provided to extend from any number of sides of two to four sides out of the four sides of the image pickup device mounting portion 25 which is in a substantially rectangular shape.

Figure 12:
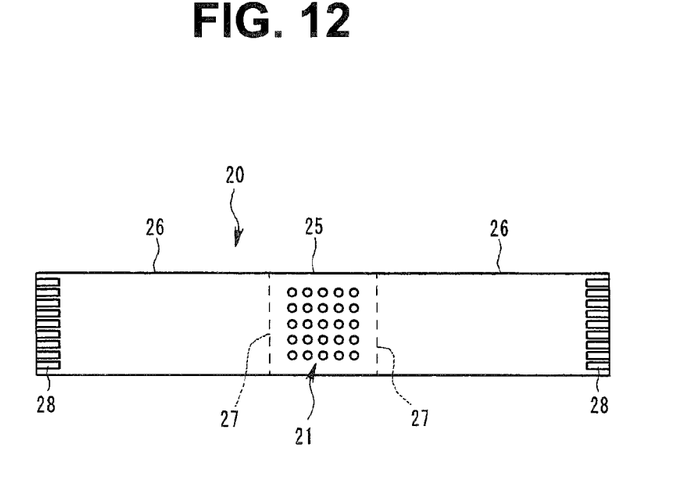
FIG. 12 is a view showing disposition of extending portions, in a second modification.
Figure 13:
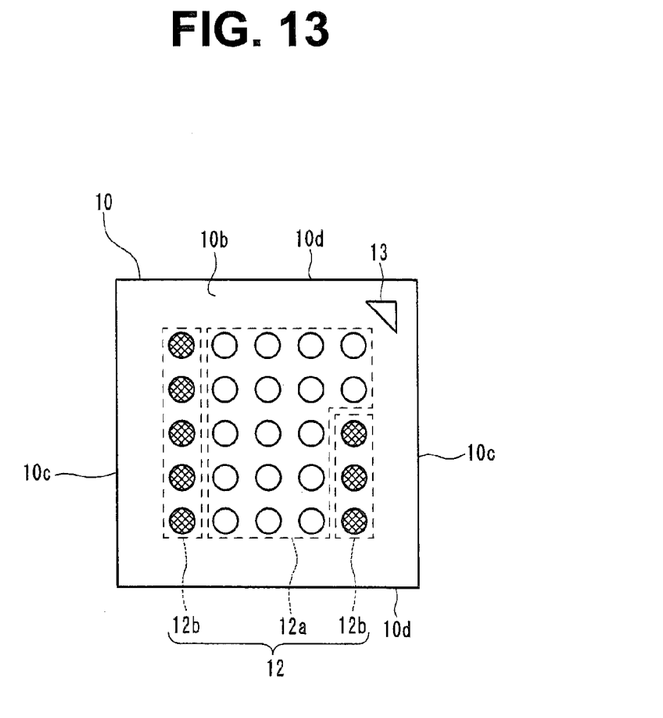
FIG. 13 is a view showing disposition of input and output terminal portions of an image pickup device, in the second modification.

For example, as shown in FIG. 12 as a second modification, a form may be adopted, in which the extending portions 26 are provided at two spots so that the extending portions 26 extend from two sides that are substantially parallel with each other out of the outer sides of the image pickup device mounting portion 25. In this case, the input and output terminal portions 12b of the image pickup device 10 are provided at an outer perimeter along the two sides 10c which are the closest to the two bent portions 27, and are substantially parallel with the bent portions 27 as shown in FIG. 13. In the second modification like this, the flexible printed wiring board 20 in the state in which the bent portions 27 are formed is in a substantially U shape.

With the first modification and the second modification described above, the aforementioned effect is obtained.

Note that the present invention is not limited to the aforementioned embodiment, and can be properly changed within the range without departing from the gist or the idea of the invention which is read from the claims and the entire description, and the endoscope image pickup unit accompanied by such a change is also included in the technical range of the present invention.

What is claimed is:

1. An endoscope image pickup unit, comprising:
   an image pickup device having a plurality of connecting terminal portions that are arranged on a back surface that is a surface at an opposite side from a light receiving surface; and
   a flexible printed wiring board including a first conductive layer and a second conductive layer on a first surface and a second surface that is opposite from the first surface, respectively,
   wherein the flexible printed wiring board comprises
   a first region in which pads to be joined to the plurality of connecting terminal portions are formed,
   a second region in which an external connection portion for connecting an electric cable is formed,
   a bent portion that is provided between the first region and the second region, and bends the flexible printed wiring board with the second surface as an inner side, and
   wirings that electrically connect the pads and the external connection portion,
   the pads comprise
   ground pads for connecting the image pickup device to a ground, and
   input and output pads that are provided closer to the bent portion than the ground pads, and are for performing input of a voltage and input and output of signals to and from the image pickup device, and
   the wirings comprise
   input and output wirings that electrically connect the input and output pads and the external connection portion, and are formed from the first conductive layer at least in the image pickup device mounting portion and the bent portion, and
   ground wirings that electrically connect the ground pads and the external connection portion, and are formed from the second conductive layer, at least in the image pickup device mounting portion and the bent portion.

2. The endoscope image pickup unit according to claim 1, wherein an outer shape of the image pickup device is a rectangular shape, the bent portion has a straight line or straight lines along one or a plurality of predetermined sides out of four outer sides of the image pickup device as a fold line or fold lines, and the input and output pads are disposed in one row along the predetermined side or sides of the image pickup device, in an outermost perimeter of a group of all the pads.

* * * * *